(12) United States Patent
Lawson et al.

(10) Patent No.: US 11,712,195 B2
(45) Date of Patent: Aug. 1, 2023

(54) DIAGNOSTIC DEVICE FOR THE IDENTIFICATION OF GERD AND DISEASES OF THE ESOPHAGUS

(71) Applicant: Nextern, Inc., White Bear Lake, MN (US)

(72) Inventors: Jonathan Lawson, Cottage Grove, MN (US); Jesse Geroy, Ham Lake, MN (US); Ken Hutchins, Cottage Grove, MN (US)

(73) Assignee: Nextern Innovation, LLC, White Bear Lake, MN (US)

( * ) Notice: Subject to any disclaimer, the term of this patent is extended or adjusted under 35 U.S.C. 154(b) by 689 days.

(21) Appl. No.: 16/788,510

(22) Filed: Feb. 12, 2020

(65) Prior Publication Data

US 2020/0253534 A1    Aug. 13, 2020

Related U.S. Application Data

(60) Provisional application No. 62/804,601, filed on Feb. 12, 2019.

(51) Int. Cl.
*A61B 5/00* (2006.01)
*A61B 1/273* (2006.01)
(Continued)

(52) U.S. Cl.
CPC ........ *A61B 5/4211* (2013.01); *A61B 1/00082* (2013.01); *A61B 1/04* (2013.01);
(Continued)

(58) Field of Classification Search
CPC ...... A61M 2210/105; A61M 2205/587; A61M 2205/3523; A61M 2205/3324;
(Continued)

(56) References Cited

U.S. PATENT DOCUMENTS 5,904,701 A * 5/1999 Daneshvar ............ A61B 17/24
                                                128/DIG. 25
6,689,056 B1   2/2004 Kilcoyne et al.
(Continued)

OTHER PUBLICATIONS

Ballon Septostomy, UT Southwestern Medical Center, n.d., [online], [retrieved on Jan. 24, 2020] Retrieved from the Internet <https://utswmed.org/conditions-treatments/balloon-septostomy/>.

(Continued)

*Primary Examiner* — Ashley K Buran
*Assistant Examiner* — Helene Bor
(74) *Attorney, Agent, or Firm* — Craige Thompson; Thompson Patent Law; Timothy D. Snowden

(57) ABSTRACT

Apparatus and associated methods relate to diagnostic device and system including a proximal balloon disposed along a length of a catheter and a distal balloon disposed at a distal end of the catheter, with at least one camera disposed at the distal balloon and a pH sensor deployable via inflation of the proximal balloon and configured to engage a patient's esophagus wall to attach the pH sensor to the patient's esophagus wall. In an illustrative example, the pH sensor may be releasably retained to the catheter adjacent to the proximal balloon. The pH sensor may include a tissue engaging feature configured to engage a patient's esophagus wall to attach the pH sensor to the patient's esophagus wall. The diagnostic device may improve upon existing processes by providing a single device to perform a multi-purpose diagnostic procedure.

20 Claims, 6 Drawing Sheets

(51) Int. Cl.
*A61B 1/04* (2006.01)
*A61B 1/00* (2006.01)
*A61B 5/145* (2006.01)
*A61B 1/06* (2006.01)
*A61M 25/10* (2013.01)

(52) U.S. Cl.
CPC .......... *A61B 1/0684* (2013.01); *A61B 1/2733* (2013.01); *A61B 5/0002* (2013.01); *A61B 5/14539* (2013.01); *A61B 5/4233* (2013.01); *A61M 25/1011* (2013.01); *A61M 2025/1015* (2013.01); *A61M 2205/3324* (2013.01); *A61M 2205/3523* (2013.01); *A61M 2205/587* (2013.01); *A61M 2210/105* (2013.01)

(58) Field of Classification Search
CPC ....... A61M 2025/1015; A61M 25/1011; A61B 5/4233; A61B 5/14539; A61B 5/0002; A61B 1/2733; A61B 1/0684; A61B 1/04; A61B 1/00082; A61B 5/4211
See application file for complete search history.

(56) References Cited

U.S. PATENT DOCUMENTS

| | | | |
|---|---|---|---|
| 10,441,759 | B2 | 10/2019 | Suehara |
| 2003/0120289 | A1* | 6/2003 | McGuckin, Jr. ..... A61B 17/072 606/139 |
| 2004/0082859 | A1* | 4/2004 | Schaer ............... A61B 18/1492 600/459 |
| 2004/0147801 | A1* | 7/2004 | Kugler .................... A61N 2/06 600/12 |
| 2004/0215128 | A1* | 10/2004 | Eerdmans .......... A61B 5/14539 604/27 |
| 2005/0149072 | A1* | 7/2005 | DeVries ........... A61B 17/00234 606/153 |
| 2005/0182342 | A1* | 8/2005 | Dinsmoor ............ A61B 5/6882 73/170.01 |
| 2005/0245788 | A1 | 11/2005 | Gerber |
| 2007/0255098 | A1* | 11/2007 | Wang ...................... A61B 1/041 600/109 |
| 2008/0029100 | A1* | 2/2008 | Glassenberg ......... A61M 16/04 128/207.15 |
| 2016/0038014 | A1* | 2/2016 | Molnar ..................... A61B 1/05 128/200.26 |

OTHER PUBLICATIONS

Uday C. Ghoshal, and Rajan Singh, Catheter-Based 24-h pH-Metry and Impedance: Technique, Interpretation, and Clinical Application, Springer Link, Evaluation of Gastrointestinal Motility and its Disorders, pp. 95-106, Oct. 25, 2016, Springer, New Delhi, [online], [retrieved on Jan. 24, 2020]. Retrieved from the Internet <https://link.springer.com/chapter/10.1007/978-81-322-0822-8_9>.

Uday C. Ghoshal, and Rajan Singh, Catheter-Based 24-h pH-Metry and Impedance: Technique, Interpretation and Clinical Application, Google Images, Springer Link, Evaluation of Gastrointestinal Motility and its Disorders, pp. 95-106, Oct. 25, 2016, Springer, New Delhi, [online], [retrieved on Jan. 24, 2020]. Retrieved from the Internet <https://www.google.com/imgres?imgurl=https%3A%2F%2Fmedia.springernature.com%2Flw785%2Fspringer-static%2Fimage%2Fchp%253A10.1007%252F978-81-322-0822-8_9%2FMediaObjects%2F307423_1_En_9_Fig4_HTML.

Wei-Yi Lei, Michael F. Vaezi, Rishi D. Naik, and Chien-Lin Chen, Mucosal impdence testing: A new diagnostic testing in gastroesopageal reflux disease, ScienceDirect, Journal of the Formosan Medical Association, Sep. 18, 2019, [online], [retrieved on Jan. 24, 2020], Retrieved from the Internet <https://www.sciencedirect.com/science/article/pii/S0929664619301469>.

Hung Cao, Vaibhav Landge, Uday Iaia, Young-Sik Seo, Smitha M. N. Rao, Shou-Jiang Tang, Harry F. Tibbals, Stuart Jon Spechler, Jung-Chih Chiao, An Implantable, Batteryless, and Wireless Capsule with Integrated Impedance and pH Sensors for Gastroesophageal Reflux Monitoring, IEEE Transactions on Biomedical Engineering, 2012, [online], [retrieved on Jan. 24, 2020]. Retrieved from the Internet <https://www.semanticscholar.org/paper/An-Implantable%2C-Batteryless%2C-and-Wireless-Capsule-Cao-Landge/.

Bravo™ Calibration-Free Reflux Testing System, Medtronic, n.d., [online], [retrieved on Jan. 24, 2020] Retrieved from the Internet <https://www.medtronic.com/covidien/en-us/products/reflux-testing/bravo-reflux-testing-system.html>.

Given Imaging International, Bravo pH Monitoring—3D Animation, YouTube, Aug. 8, 2011, [online], [retrieved on Jan. 24, 2020], Retrieved from the Internet <https://www.youtube.com/watch?v=AA-qzQAfLDs>.

Ana-Maria Singeap, Carol Stanciu, and Anca Trifan, Capsule endoscopy: The road ahead, World Journal of Gastroenterology, 22(1): 369-378, Jan. 7, 2016, [online], [retrieved on Jan. 24, 2020]. Retrieved from the Internet <https://www.ncbi.nlm.nih.gov/pmc/articles/PMC4698499/>.

Gastone Ciuti, R. Calio, D. Camboni, L. Neri, F. Bianchi, A. ARF770, A. Koulaouzidis, S. Schostek, D. Stoyanov, C. M. Oddo, B. Magnani, A. Menciassi, M. Morino, M. O. Schurr, and P. Dario, Frontiers of robotic endoscopic capsules: a review, Journal of Micro-Bio Robotics, 11(1): 1-18, May 2, 2016, [online], [retrieved or Jan. 24, 2020]. Retrieved from the Internet <https://www.ncbi.nlm.nih.gov/pmc/articles/PMC5646258/>.

Guardian Endoscope Single-Use Valve Set, Olympus America: Medical, n.d., [online], [retrieved on Jan. 24, 2020]. Retrieved from the Internet <https://medical.olympusamerica.com/products/guardian-endoscope-single-use-valve-set>.

\* cited by examiner

DIAGNOSTIC DEVICE FOR THE IDENTIFICATION OF GERD AND DISEASES OF THE ESOPHAGUS

CROSS-REFERENCE TO RELATED APPLICATIONS

This application also claims the benefit of U.S. Provisional Application Ser. No. 62/804,601, titled "DIAGNOSTIC DEVICE FOR THE IDENTIFICATION OF GERD AND DISEASES OF THE ESOPHAGUS," filed by Jonathan Lawson, et al., on Feb. 12, 2019.

This application incorporates the entire contents of the foregoing application(s) herein by reference.

TECHNICAL FIELD

Various embodiments relate generally to systems and methods for the identification of gastro esophageal reflux disease (GERD), Barrett's Esophagus (BE) and other diseases of the esophagus and gastro intestinal (GI) tract.

BACKGROUND

Gastroesophageal reflux disease (GERD), also known as acid reflux, occurs when stomach acid frequently flows back into the esophagus, and may irritate the lining of the esophagus. Symptoms of GERD include the taste of acid in the back of the mouth, heartburn, bad breath, chest pain, regurgitation, breathing problems, and wearing away of the teeth. Complications of GERD include esophagitis, esophageal stricture, and Barrett's esophagus (BE). Risk factors include obesity, pregnancy, smoking, hiatal hernia, and taking certain medicines. Treatment options include lifestyle changes, medications, and sometimes surgery for those who do not improve with the first two measures. By some measures, between 10 and 20% of the population of the Western world is affected by GERD.

A doctor might be able to diagnose GERD based on a physical examination and history of symptoms. To confirm a diagnosis of GERD, or to check for complications, a doctor might recommend an upper endoscopy, an ambulatory acid (pH) probe test, an esophageal manometry, and/or an x-ray of the upper digestive system. Under a typical upper endoscopy procedure, a doctor may insert a thin, flexible tube equipped with a light and camera (endoscope) down the throat, to examine the inside of the esophagus and stomach. Various companies (such as Olympus®) may sell reusable endoscopes that are used to visually inspect the esophageal lining for indications of BE. Some companies may distribute one-time use sensors that are configured to attached to the esophagus to monitor pH levels and wirelessly transmit data to an external recorder (see, e.g., the Medtronic® Bravo™ pH sensor). Other companies may sell wired pH sensors that are placed with the sensor in the esophagus and a wire running trans-nasally to a body worn recorder. The PillCam™ device (also made by Medtronic®) is designed for visual inspection of the GI tract for signs of disease.

SUMMARY

Apparatus and associated methods relate to diagnostic device and system including a proximal balloon disposed along a length of a catheter and a distal balloon disposed at a distal end of the catheter, with at least one camera disposed at the distal balloon and a pH sensor deployable via inflation of the proximal balloon and configured to engage a patient's esophagus wall to attach the pH sensor to the patient's esophagus wall. In an illustrative example, the pH sensor may be releasably retained to the catheter adjacent to the proximal balloon. The pH sensor may include a tissue engaging feature configured to engage a patient's esophagus wall to attach the pH sensor to the patient's esophagus wall. The diagnostic device may improve upon existing processes by providing a single device to perform a multi-purpose diagnostic procedure.

Various embodiments may achieve one or more advantages. For example, some embodiments may eliminate a need to pass two distinct instruments (e.g., separate endoscope and pH sensor) independently to perform a diagnosis. The diagnostic system may beneficially aid in the identification of gastro esophageal reflux disease (GERD) and other various diseases of the esophagus. The diagnostic device may also be specifically designed and optimized to be placed without the need to intubate the patient. In some situations, failure of the lower esophageal sphincter (LES) to completely close can lead to acid entering the esophagus, particularly when the individual is laying down. While GERD is commonly diagnosed by monitoring pH in the esophagus, left untreated, the acid can erode the esophageal lining, leading to a BE, which is a precursor to cancer. Diagnosis of BE is often done visually, using an endoscope. Accordingly, the diagnostic system disclosed herein may beneficially be used to search for signs of both GERD, BE and other diseases, conditions, or complications of the esophagus, using a single compact diagnostic system and associated procedure.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

Figure 1:
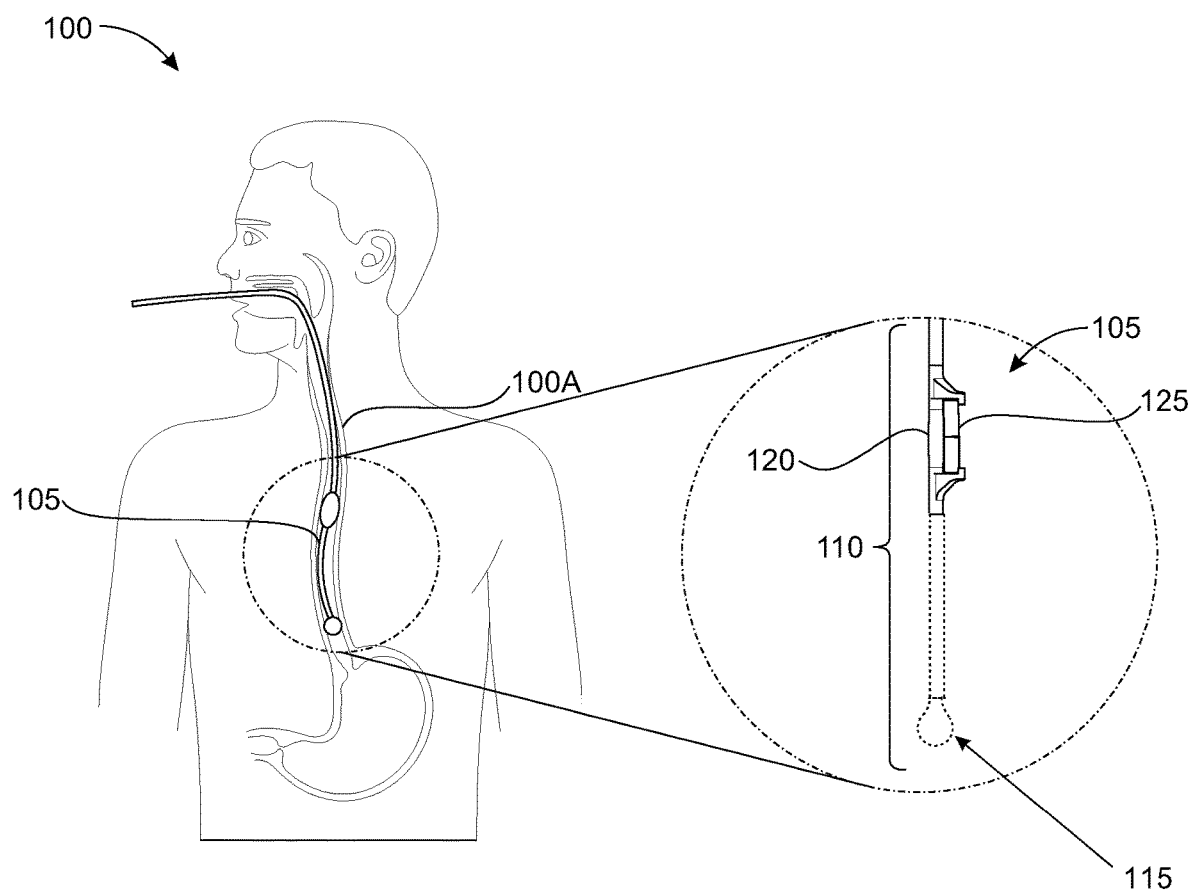
FIG. 1 depicts a perspective view of a patient being diagnosed for gastroesophageal reflux disease (GERD) using an exemplary two-balloon catheter system configured as a combined endoscope and pH sensor apparatus.

FIG. 1 depicts a perspective view of a patient being diagnosed for gastroesophageal reflux disease (GERD) using an exemplary two-balloon catheter system configured as a combined endoscope and pH sensor apparatus. A human patient 100 may have entered a doctor's office to undergo a diagnosis for esophageal disease. Like any other human, the patient 100 has an esophagus 100A through which food consumed by the patient 100 may pass to reach the stomach for digestion. The patient's esophagus 100A may be affected by various diseases, conditions, or complications, such as gastric reflux, cancer, dysphagia, odynophagia, gastroesophageal reflux disease (GERD), esophagitis, esophageal stricture, and/or Barrett's esophagus (BE). To diagnose at least some of these issues, a doctor may utilize an exemplary two-balloon catheter system 105, which functions as a combined endoscope and pH sensor to more efficiently perform esophagus inspection and monitoring procedures. To illustrate further, as shown on the right of FIG. 1, a zoomed-in view of the catheter system 105 includes a longitudinally extending catheter (shaft) 110. The catheter 110 has an inflatable camera balloon 115 located at a distal end of the catheter 110. The camera balloon 115 includes a camera (not shown) configured to perform visual inspections for indications or signs of BE. The catheter system 105 further includes a proximal balloon 120 configured to inflate to deploy a pH sensor 125. The pH sensor may be deployed at a point along an internal wall of the patient's esophagus 100A for the detection of pH levels to possibly diagnose GERD in the patient 100. The two balloon catheter system 100 may therefore advantageously eliminate a need to pass two different instruments (e.g., separate endoscope and pH sensor) independently to perform a diagnosis procedure. Additionally, the dual-function catheter device 105 may be designed to be placed without the need to intubate the patient, thus allowing for a wider range of possible use applications for the system 105.

Figure 2:
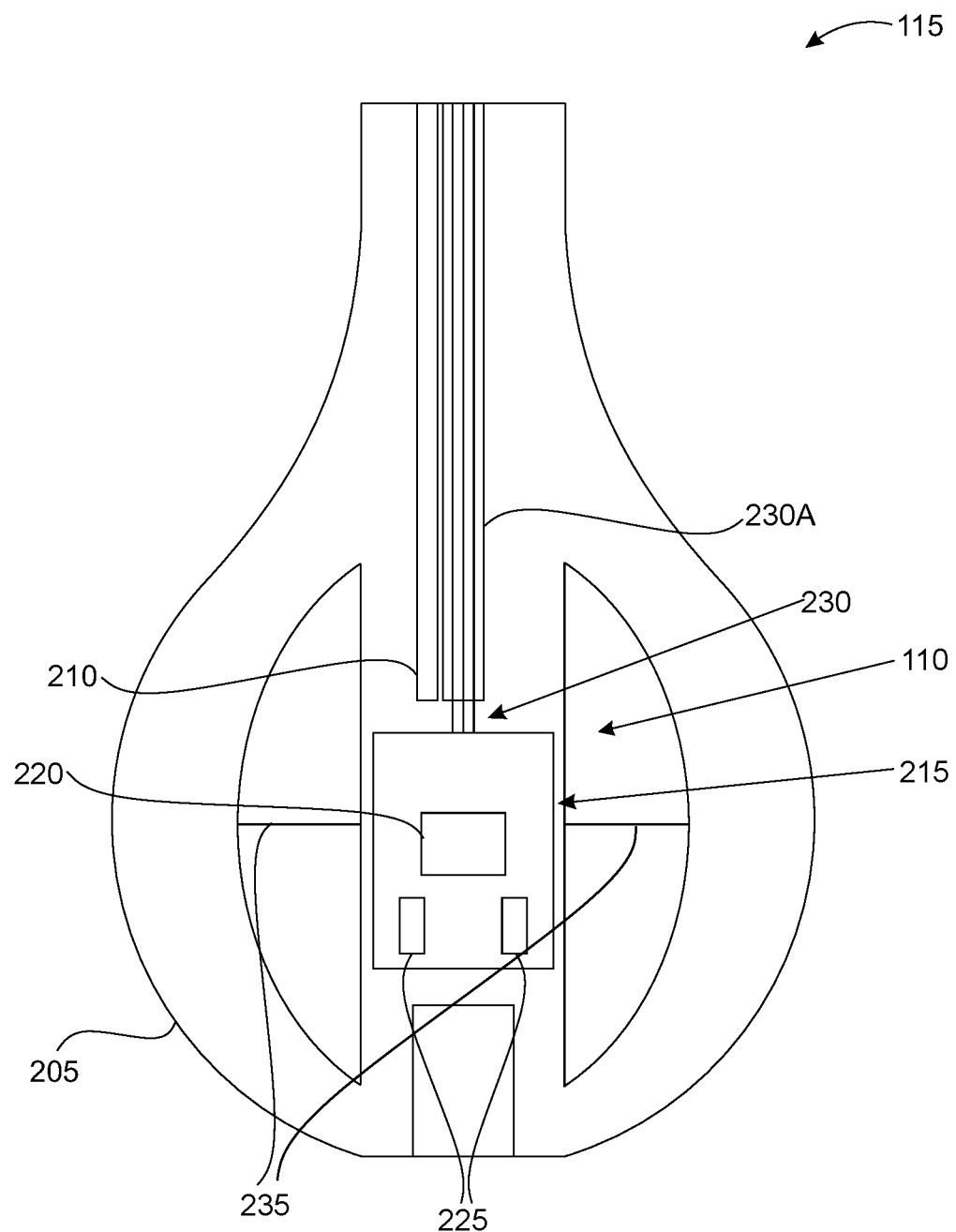
FIG. 2 depicts a cross-sectional view of an exemplary distal camera balloon of an exemplary two-balloon catheter system.

FIG. 2 depicts a cross-sectional view of an exemplary distal camera balloon of an exemplary two-balloon catheter system. The distal (camera) balloon 115 includes an inflatable balloon 205. The balloon 115 is inflatable via an inflation lumen 210 that extends through the catheter 110 to be in fluid communication with an external pressure source (e.g., a balloon pump). Contained within the distal balloon 205 is an imaging camera electronics substrate 215. Some examples may have the substrate 215 mounted inside the distal balloon 115 on a balloon catheter (shaft) 110. Coupled to the substrate 215 is at least one imaging camera 220 and at least one lighting source 225 (e.g., a light emitting diode (LED)). In an exemplary embodiment, a catheter system 100 may include a camera and two LEDs on each opposing surface of the substrate 215 (e.g., the opposite side of the substrate 215 may be a mirror image of the substrate 215 as shown in FIG. 2). Put another way, one camera 220 may be located on each opposing side of the central catheter shaft 110. In such implementations, the two oppositely-facing image sensors 220 are designed such that there is a sensor on either side of the catheter body, providing a full 360-degree view using the distal camera balloon 115.

The camera(s) 220 and light source(s) 225 may receive operating power and transmit/receive data via electrical wiring 230 extending through an electrical conduit lumen 230A of the catheter shaft 110. The distal balloon 115 may further include an alignment indicia 235. The camera(s) 220 in the balloon 115 may be used to visualize and align the balloon 115 with a patient's squamo-columnar junction, where the alignment indicia 235 (e.g., a fixed visible horizontal line in the balloon 115) may be used to assist in finding the proper location. In some examples, the balloon 115, catheter 110, the substrate 215, and the camera 220 may be sized such that the system 105 can be passed trans-nasally (or even potentially swallowed by the patient 100). In various examples, the surface(s) of the substrate 215 may be potted, or otherwise sealed in a sealing material to form a lens for the imaging sensor(s) 220. Furthermore, because the system 105 may include sensors 220 and LEDs 225 pointing 180 degrees apart, a full 360-degree field of view can be observed via the camera balloon 205 without rotating the catheter system 105.

Once in the esophagus 110A, the distal camera balloon 115 is dilated (via the inflation lumen 210). Dilation of the balloon 115 expands the esophagus 110A to a predetermined spatial dimension to provide an appropriate focal length for the camera 220 of the balloon 115. The balloon 115 may be inflated with gas or a fluid (having an appropriate refraction index) to minimize reflection from the interior of the balloon 115.

Figure 3A:
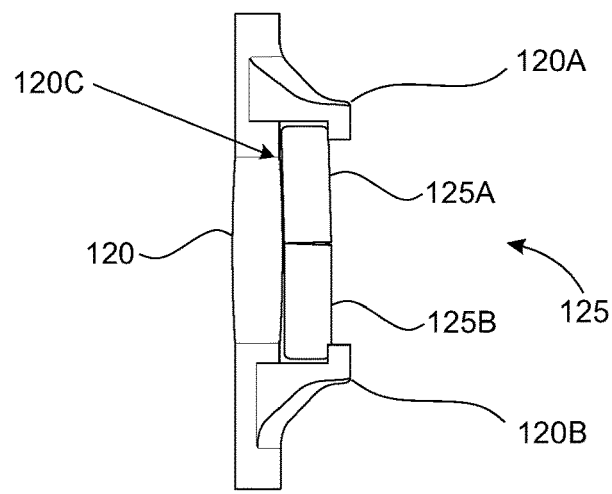
FIGS. 3A-3F depict various views of an exemplary deployment of an exemplary pH sensor of a two-balloon catheter system.

FIGS. 3A-3F depict various views of an exemplary deployment of an exemplary pH sensor of a two-balloon catheter system. FIG. 3A depicts the pH sensor 125 loaded into the catheter 110, ready for insertion. The sensor 125 is deployingly retained to the catheter 110 via a pair of retention members 120A, 120B fixed to the catheter 110 to define a sensor holder or receptacle 120C that is occupied by the sensor 125 (as shown in FIG. 3A). The pH sensor 125, in this illustrative depiction, is of a two-piece construction, having a first sensor piece or member 125A, and a second sensor piece or member 125B. The sensor pieces 125A, 125B may be hinged to each other at hinge point 125D, which may be a biased hinge configured to bias the two sensor portions 125A, 125B into physical engagement with one another (as shown in FIG. 3A).

Figure 3B:
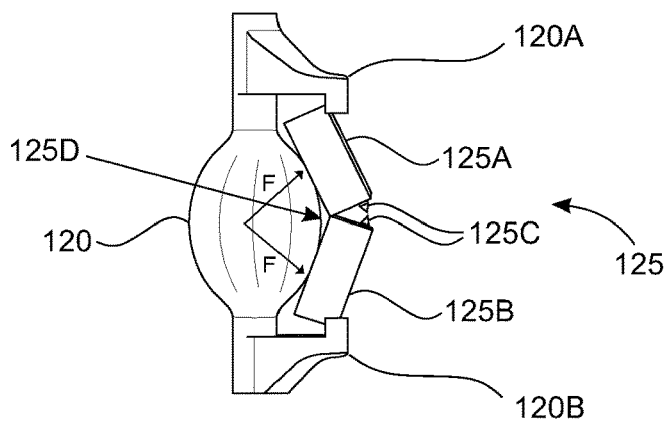
Figure 3C:
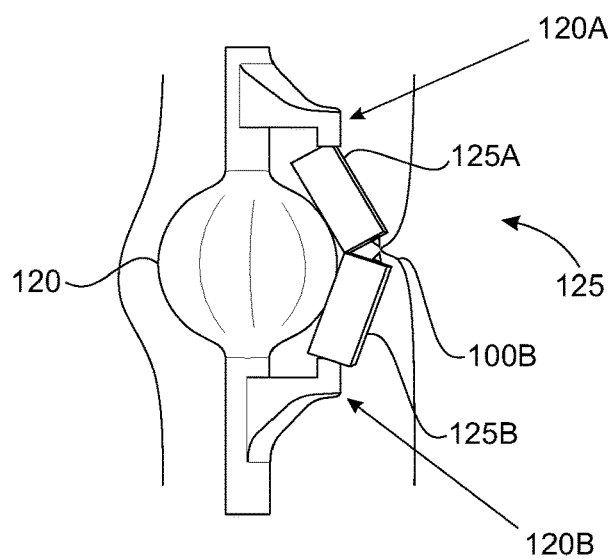
Figure 3D:
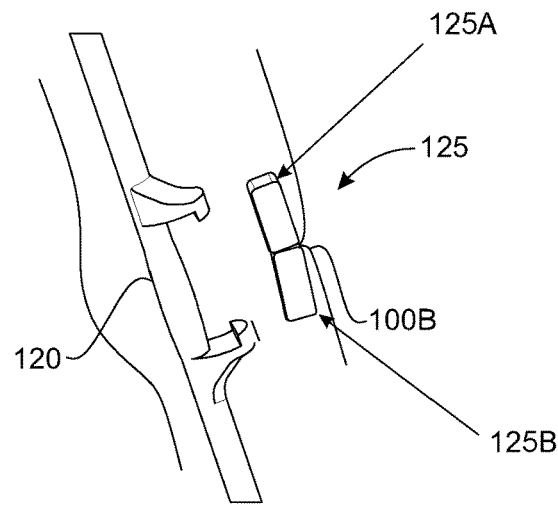
Figure 3E:
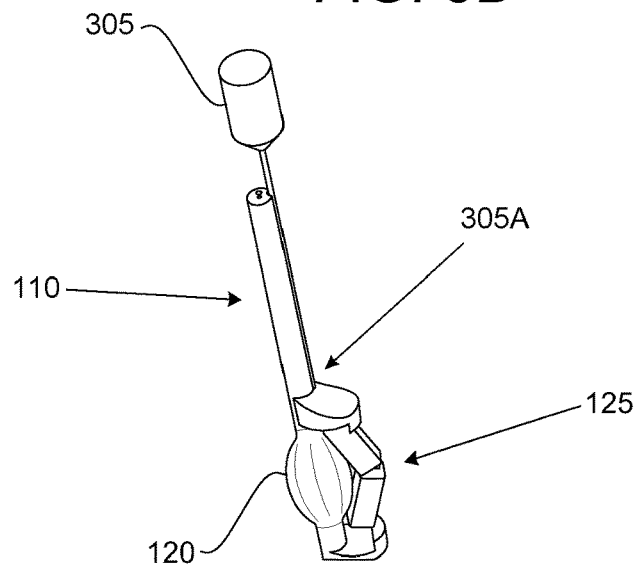
Figure 3F:
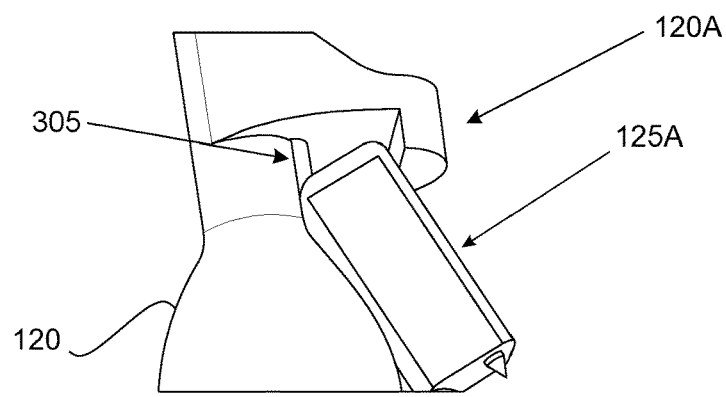

FIG. 3B shows the system 105 after insertion, where the proximal balloon is (partially) inflated, causing tissue engaging feature(s) 125C (e.g., teeth) of the sensor 125 to become exposed. As shown in FIG. 3C, the inflation of the balloon 120 forces (via outwardly radially directed forces F) the exposed teeth 125C of the sensor pieces 125A, 125B into contact with an esophagus wall 100B associated with the esophagus 100A of the patient. As the pH sensor 125 snaps back together when it becomes free of the catheter 120 (due to the spring-bias at the hinge point 125D and deflation of the proximal balloon 120), the sensor 125 will attach to the esophagus wall 100B, as seen in FIG. 3D. In some examples, the sensor 125 may be physically forced out of the catheter 110 using a (semi-) rigid member, such as a stylet 305 (as seen in FIG. 3E), such that the distal end of the stylet 305 is configured to forceably engage with the first piece 125A of the sensor 125 (as seen in FIG. 3F) to eject the sensor 125 from the sensor retention receptacle 120C. For example, the stylet 305 may be inserted fully (or partially) through an ejection channel or lumen 310 of the catheter 110, which may also stiffen the catheter 110 for ease of deployment down the patient's esophagus 100A.

After the catheter 110 is withdrawn, the sensor 125 wirelessly transmits data to an external device (e.g., a body worn device, In some implementations. In various examples, the sensor 125 may be attached via a wire running from the sensor 125, up the patient's esophagus 100A, through the patient's nose, and then finally to the external device. The data may be received at the external device and transmitted to another device, such as the patient's smartphone, for transmission to a central server, or directly from the device through the patient's Wi-Fi network. The device may, in some implementations, be physically sent to a health care facility for review of the transmitted data. The sensor 125 may be configured to transmit data to a patient device, such as a smartphone for collation and transfer to a monitoring station/central server.

Figures 4, 5:
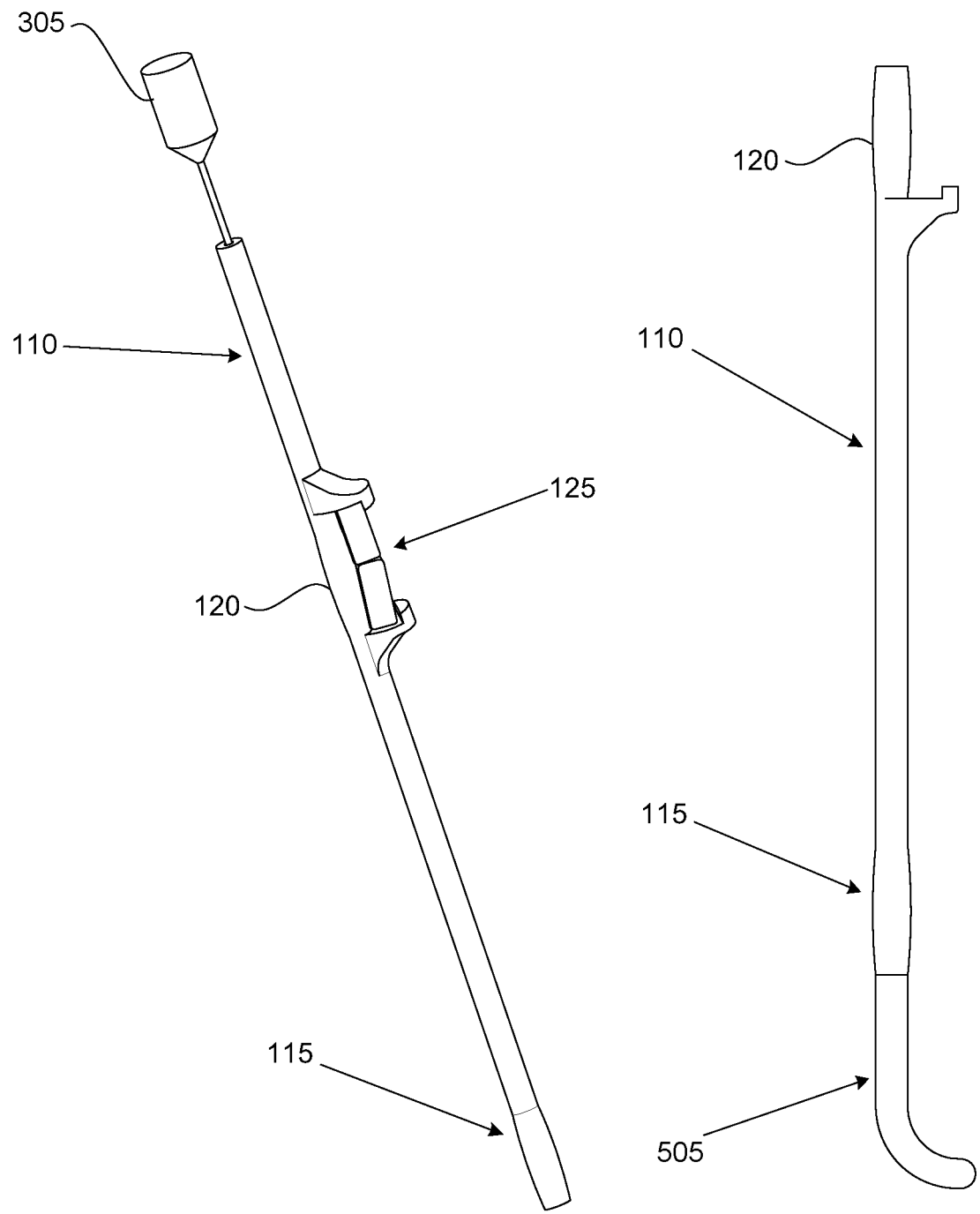
FIG. 4 depicts a perspective view of an exemplary two balloon catheter system with a deployment stylet.
FIG. 5 depicts a side elevation view of an exemplary two balloon catheter system with an exemplary flexible catheter tip extending past the exemplary distal camera balloon.

FIG. 4 depicts a perspective view of an exemplary two balloon catheter system with a deployment stylet.

FIG. 5 depicts a side elevation view of an exemplary two balloon catheter system with an exemplary flexible catheter tip extending past the exemplary distal camera balloon. In this depicted example, the catheter 110 includes a distal end flexible tip 505 that extends past the distal balloon. The flexible tip 505 may be controllable via a proximal end of the catheter 110, in accordance with various flexible catheter tip deflection systems and techniques known in the art.

Figure 6:
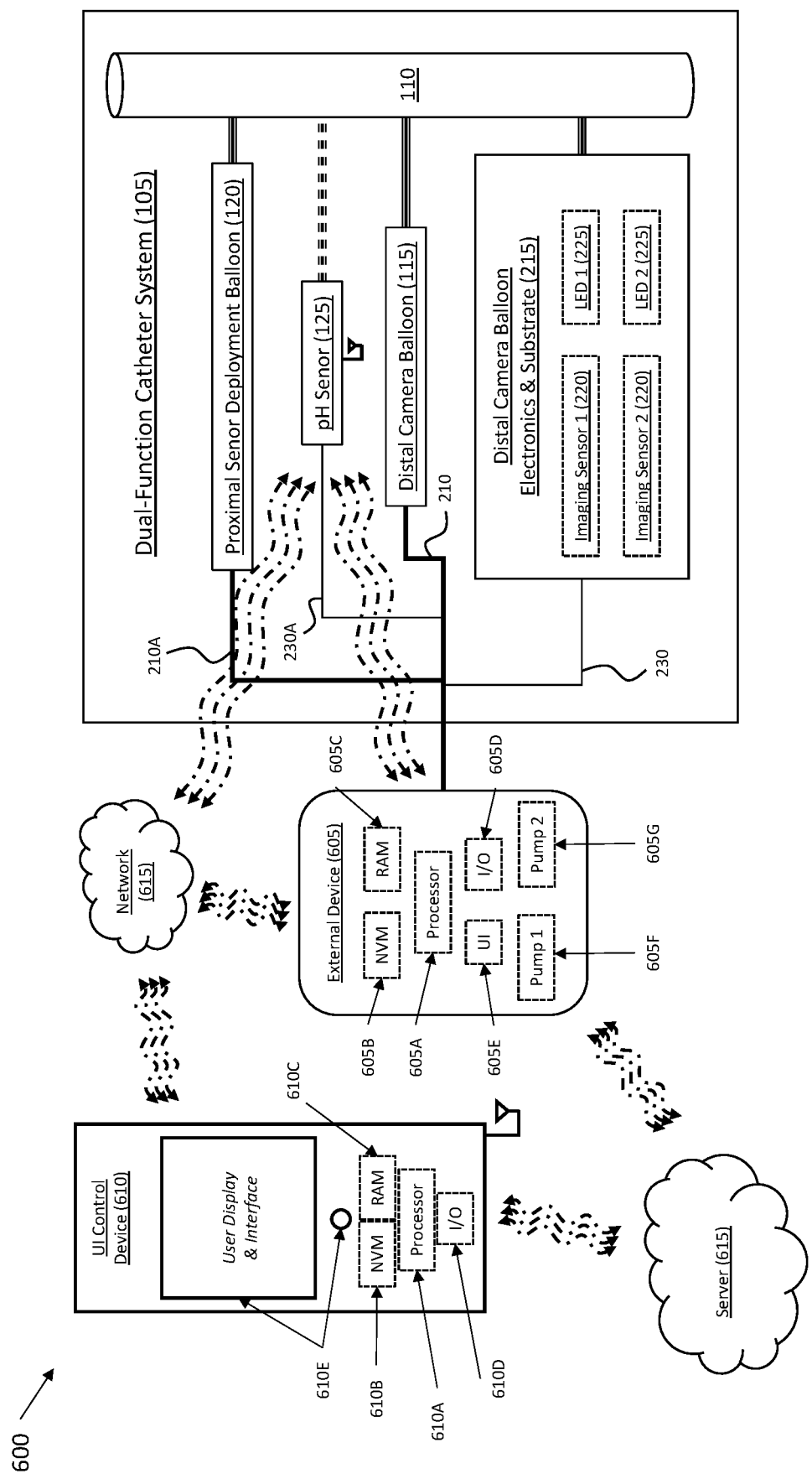
FIG. 6 depicts a block-diagram view of an exemplary two-balloon catheter system interfacing with supporting devices and components.

FIG. 6 depicts a block-diagram view of an exemplary two-balloon catheter system interfacing with supporting devices and components. As described above, a dual-function catheter system 105 includes a catheter member or shaft 110, a distal camera balloon 115, a proximal (pH) sensor deployment balloon 120, and distal balloon electronics and substrate 215. The distal balloon electronics and substrate 215 includes an opposing pair of imaging sensors 220 and an opposing pair of LEDs 225 for full 360 degree lighting and visibility. The components of the system 105 are operably coupled to an external device 605. The external device 605 may include a number of components, including, for example, a processor 605A, non-volatile memory 605B, volatile memory 605C, input/output 605D, user interface 605E, a first (liquid) pump 605F, and a second (gas) pump 605G. The external device is operable to control and interface with the components of the system 105. For example, the balloons 115, 120 may be individually and fluidly coupled to one of the associated pumps 605F, 605G (via pressure lumens or lines 210 and 210A, respectively), such that the device 605 is configured to selectively control inflation and deflation of the balloons 115 and 120. The distal camera balloon electronics and substrate 215 is also coupled (electrically) to the external device 605 via electrical wires 230, such that the device 605 is configured to receive camera or video data from the imaging sensors 220, as well as control a level of luminance of the LEDs 225. In various embodiments, the pH sensor 125 may also be coupled (e.g., hardwired) to the external device 605 via wiring 230A, such that the sensor 125 may be configured to deliver sensor readings to the device 605 over a reliable wired connection. In various examples the pH sensor 125 may include its own internal electronics (e.g., processor, memory, I/O, wireless interface), such that the sensor 125 may be configured to wirelessly transmit/receive data to/from various external devices.

In various examples, the sensor 125 may be attached via a wire running from the sensor 125, up the patient's esophagus 100A, through the patient's nose, and then finally to the external device. The data may be received at the external device 605 and transmitted to another device, such as the patient's smartphone 610, for transmission to a central server 615, or directly from the device through the patient's Wi-Fi network 620. The device may, in some implementations, be physically sent to a health care facility for review of the transmitted data. The sensor 125 may be configured to transmit data to a patient device, such as the smartphone 610 (including, for example, a processor 610A, non-volatile memory 610B, volatile memory 610C, input/output 610D, and user interface 610E) for collation and transfer to a monitoring station/central server 615.

An exemplary method of using an exemplary two-balloon catheter system may include placement of a pH sensor 125 (e.g., orally or transnasally). In order to place the sensor, an endoscope 115 may be used to determine the desired location for the capsule in the esophagus. The sensor 125 may be placed about 6 cm (2.4 inches) above the squamo-columnar junction, which is identified visually using the endoscope 115. A clinician may measure and record the distance traveled by the endoscope 115 to the desired location, remove the endoscope 115 and then pass the sensor 125. The balloon 125 may be inflated to a slightly larger diameter, locking the catheter system 100 in place. The camera in the balloon can be used to visualize and align the balloon with the squamo-columnar junction. The pH sensor 125 may be mounted about 6 cm proximal to the alignment indicia 235 of the balloon 115. Once the catheter 110 is locked in place by inflating the camera balloon 115, the pH sensor 125 can be deployed. The sensor 125 may be mounted on a second, more proximal balloon 120, such that when inflated, the balloon 120 causes the sensor 125 to engage a sidewall 100B of the esophagus 100A. A secondary action, such as the insertion of a stylet 305, may cause the sensor 125 to dismount from the catheter 110. The secondary action may be the deflation of the proximal balloon 120, in some examples. All balloons may be deflated to remove the catheter 110, leaving the sensor 125 behind for delivering valuable sensor measurements.

Although various embodiments have been described with reference to the Figures, other embodiments are possible. For example, a catheter body for a swallowable device version of the catheter system 100 may be small and flexible. For example, catheter body may be as flexible as a string, and the catheter balloon could be the size of a large multivitamin (e.g., about 0.05 to 0.1 inches cubed in volume). In such a swallowable device application, the balloon 115 may first be swallowed, and the catheter balloon 115 then slightly inflated, providing a field of view for the camera(s) 220. The catheter body may be used to pull the balloon into the esophagus 100A from the stomach, and a clinician can then view the esophagus as the balloon is slowly withdrawn up the esophagus.

In a transnasal version of the catheter system 100, the catheter body may be stiff to allow for push-ability. The additional stiffness may allow a clinician to view the esophagus 100A while advancing and retracting the catheter 110. A stylet 305 may be used to vary the stiffness, allowing the catheter distal end to be more flexible as it is passed through the nasal passage and into the esophagus when it is withdrawn. Advancing the stylet 305 may stiffen the catheter, providing better control when advancing and manipulating the catheter system 100. The transnasal version may be substantially similar to the swallowable version, but with the addition of the stylet 305. Another method to achieve the stiffness required for push-ability would be through the braid in the tubing instead of a stylet.

A diagnostic device may be used for the identification of gastro esophageal reflux disease (GERD) and diseases of the esophagus. The diagnostic device may include a longitudinally extending catheter. The diagnostic device may include a proximal balloon located along a length of the catheter. The diagnostic device may include a distal balloon located at a distal end of the catheter. The diagnostic device may include at least one camera located at the distal balloon. The diagnostic device may include at least one light source located at the distal balloon. The diagnostic device may include a pH sensor deployable via inflation of the proximal balloon and configured to engage a patient's esophagus wall to attach the pH sensor to the patient's esophagus wall.

In various examples, the pH sensor may be releasably retained to the catheter adjacent to the proximal balloon. The pH sensor may, in some examples, include a tissue engaging feature configured to engage a patient's esophagus wall to attach the pH sensor to the patient's esophagus wall. The tissue engaging feature may be at least two teeth, in various implementations. The pH sensor may include a first sensor piece and a second sensor piece. The second sensor piece may be configured in a hinge relationship with the first sensor piece. In some examples, a first tooth of the at least two teeth may be located at the first sensor piece, while a second tooth of the at least two teeth may be located at the second sensor piece. Inflation of the proximal balloon may cause the tissue engaging feature of the pH sensor to become exposed, such that a deployment force of the balloon may be configured to force the exposed teeth into contact with the patient's esophagus wall, and the first and second sensor pieces may be configured to snap together to engage the patient's esophagus wall when the pH sensor is freely deployed from the catheter by the deployment force of the balloon.

In some implementations, the at least one camera may include two cameras each oriented 180 degrees relative to one another to provide for a full 360 degree field of view of the at least one camera. The at least one light source may be two light emitting diodes (LEDs) oriented 180 degrees relative to one another to provide for a full 360 degree field of lighting of the at one light source. The diagnostic device may further include a stylet having a distal end configured to forcingly deploy the pH sensor from catheter. The diagnostic device may further include a stylet configured to be received in the catheter to stiffen the catheter for insertion into the patient's esophagus wall. The diagnostic device may further include a distal flexible tip extending distally past the distal balloon and from the distal end of the catheter. The pH sensor may be configured to wirelessly transmit sensor data to an external device, in some examples. The pH sensor is configured to transmit sensor data to an external device over a wired connection, in various applications.

Some aspects of embodiments may be implemented as a computer system. For example, various implementations may include digital and/or analog circuitry, computer hardware, firmware, software, or combinations thereof. Apparatus elements can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Some embodiments may be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example and not limitation, both general and special purpose microprocessors, which may include a single processor or one of multiple processors of any kind of computer. Generally, a processor will receive instructions and data from a read-only memory or a random-access memory or both. The essential elements of a computer are a processor for executing instructions and one or more memories for storing instructions and data. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits). In some embodiments, the processor and the memory can be supplemented by, or incorporated in hardware programmable devices, such as FPGAs, for example.

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. An exemplary embodiment may be implemented in a computer system that includes a graphical user interface and/or an Internet browser. To provide for interaction with a user, some implementations may be implemented on a computer having a display device, such as an LCD (liquid crystal display) monitor for displaying information to the user, a keyboard, and a pointing device, such as a mouse or a trackball by which the user can provide input to the computer.

In various implementations, the system may communicate using suitable communication methods, equipment, and techniques. For example, the system may communicate with compatible devices (e.g., devices capable of transferring data to and/or from the system) using point-to-point communication in which a message is transported directly from a source to a receiver over a dedicated physical link (e.g., fiber optic link, infrared link, ultrasonic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, and the computers and networks forming the Internet. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, FireWire, ATA/IDE, RS-232, RS-422, RS-485, 802.11 a/b/g/n, Wi-Fi, WiFi-Direct, Li-Fi, BlueTooth, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

In various embodiments, a computer system may include non-transitory memory. The memory may be connected to the one or more processors, which may be configured for storing data and computer readable instructions, including processor executable program instructions. The data and computer readable instructions may be accessible to the one or more processors. The processor executable program instructions, when executed by the one or more processors, may cause the one or more processors to perform various operations.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are within the scope of the following claims.

What is claimed is:

1. A diagnostic device for the identification of gastro esophageal reflux disease (GERD) and diseases of the esophagus, the diagnostic device comprising:
   a longitudinally extending catheter;
   a proximal balloon disposed along a length of the catheter;
   a distal balloon disposed at a distal end of the catheter;
   at least one camera disposed at the distal balloon;
   at least one light source disposed at the distal balloon; and,
   a pH sensor disposed over and exterior to the proximal balloon, actuated via inflation of the proximal balloon, and configured to engage a patient's esophagus wall to attach the pH sensor to the patient's esophagus wall, wherein the pH sensor is releasably retained to the catheter adjacent to the proximal balloon.

2. The diagnostic device of claim 1, wherein the pH sensor comprises a tissue engaging feature configured to engage a patient's esophagus wall to attach the pH sensor to the patient's esophagus wall.

3. The diagnostic device of claim 2, wherein the tissue engaging feature comprises at least two teeth.

4. The diagnostic device of claim 3, wherein:
   the pH sensor comprises a first sensor piece and a second sensor piece,
   the second sensor piece is configured in a hinge relationship with the first sensor piece,
   a first tooth of the at least two teeth is disposed at the first sensor piece, and,
   a second tooth of the at least two teeth is disposed at the second sensor piece.

5. The diagnostic device of claim 4, wherein inflation of the proximal balloon causes the tissue engaging feature of the pH sensor to become exposed, such that a deployment force of the balloon is configured to force the exposed teeth into contact with the patient's esophagus wall, and wherein the first and second sensor pieces are configured to snap together to engage the patient's esophagus wall when the pH sensor is freely deployed from the catheter by the deployment force of the balloon.

6. The diagnostic device of claim 1, wherein the at least one camera comprises two cameras each oriented 180 degrees relative to one another to provide for a full 360 degree field of view of the at least one camera.

7. The diagnostic device of claim 6, wherein the at least one light source comprises two light emitting diodes (LEDs) oriented 180 degrees relative to one another to provide for a full 360 degree field of lighting of the at one light source.

8. The diagnostic device of claim 1, further comprising a distal flexible tip extending distally past the distal balloon and from the distal end of the catheter.

9. The diagnostic device of claim 1, wherein the pH sensor is configured to wirelessly transmit sensor data to an external device.

10. The diagnostic device of claim 1, wherein the pH sensor is configured to transmit sensor data to an external device over a wired connection.

11. A diagnostic device for the identification of gastro esophageal reflux disease (GERD) and diseases of the esophagus, the diagnostic device comprising:
    a longitudinally extending catheter;
    a proximal balloon disposed along a length of the catheter;
    a distal balloon disposed at a distal end of the catheter;
    at least one camera disposed at the distal balloon;
    at least one light source disposed at the distal balloon;
    a pH sensor disposed over and exterior to the proximal balloon, actuated via inflation of the proximal balloon, and configured to engage a patient's esophagus wall to attach the pH sensor to the patient's esophagus wall.

12. The diagnostic device of claim 11, wherein the at least one camera comprises two cameras each oriented 180 degrees relative to one another to provide for a full 360 degree field of view of the at least one camera.

13. The diagnostic device of claim 11, wherein the at least one light source comprises two light emitting diodes (LEDs) oriented 180 degrees relative to one another to provide for a full 360 degree field of lighting of the at one light source.

14. The diagnostic device of claim 11, further comprising a stylet having a distal end configured to forcingly deploy the pH sensor from catheter.

15. The diagnostic device of claim 11, further comprising a distal flexible tip extending distally past the distal balloon and from the distal end of the catheter.

16. The diagnostic device of claim 11, wherein the pH sensor is configured to wirelessly transmit sensor data to an external device.

17. The diagnostic device of claim 11, wherein the pH sensor is configured to wirelessly transmit sensor data to an external device.

18. The diagnostic device of claim 11, wherein the pH sensor is configured to transmit sensor data to an external device over a wired connection.

19. A diagnostic device for the identification of gastro esophageal reflux disease (GERD) and diseases of the esophagus, the diagnostic device comprising:
    a longitudinally extending catheter;
    a proximal balloon disposed along a length of the catheter;
    a distal balloon disposed at a distal end of the catheter;
    at least one camera disposed at the distal balloon;
    at least one light source disposed at the distal balloon; and,
    a means for pH sensing disposed over and exterior to the proximal balloon, actuated via inflation of the proximal balloon, and configured to engage a patient's esophagus wall to attach the means for pH sensing to the patient's esophagus wall.

20. The diagnostic device of claim 19, wherein:
    the at least one camera comprises two cameras each oriented 180 degrees relative to one another to provide for a full 360 degree field of view of the at least one camera, the at least one light source comprises two light emitting diodes (LEDs) oriented 180 degrees relative to one another to provide for a full 360 degree field of lighting of the at one light source.

\* \* \* \* \*